United States Patent [19]
Robertson

[11] Patent Number: 6,099,458
[45] Date of Patent: Aug. 8, 2000

[54] ENCAPSULATED LOW-ENERGY BRACHYTHERAPY SOURCES

[76] Inventor: Robert Robertson, 503-51 Hasting Rd., Dollard des Ormeaux, Quebec, Canada, H9G 1Y3

[21] Appl. No.: 09/248,099

[22] Filed: Feb. 11, 1999

Related U.S. Application Data

[60] Provisional application No. 60/074,550, Feb. 12, 1998.
[51] Int. Cl.[7] ............................. A61M 36/00; A61N 5/00
[52] U.S. Cl. ...................................... 600/8; 600/3
[58] Field of Search ............................. 600/1–8

[56] References Cited

U.S. PATENT DOCUMENTS

| | | |
|---|---|---|
| 1,753,287 | 4/1930 | Failla . |
| 3,351,049 | 11/1967 | Lawrence . |
| 4,323,055 | 4/1982 | Kubiatowicz . |
| 4,702,228 | 10/1987 | Russell, Jr. et al. . |
| 4,891,165 | 1/1990 | Suthanthiran . |
| 4,994,013 | 2/1991 | Suthanthiran et al. . |
| 5,342,283 | 8/1994 | Good . |
| 5,405,309 | 4/1995 | Carden, Jr. . |
| 6,007,475 | 12/1999 | Slater et al. ................. 600/8 |

OTHER PUBLICATIONS

"Instertital Brachytherapy—Physical and Clinical Consideration", Interstitial Collaborative Working Group, Raven Press, New York (1990), ISBN 0–882167–581–4 Medical Physics, vol. 19, No. 4, pp. 927–931 (1992).

*Primary Examiner*—Cary O'Connor
*Assistant Examiner*—Catherine E McPherson
*Attorney, Agent, or Firm*—Smith Gambrell & Russell, LLP

[57] ABSTRACT

An essentially cylindrical, metal-encapsulated, brachytherapy source including an outer metal capsule, an annulus in a central interior position of said outer metal capsule, and a longitudinally extending heavy metal core in said annulus. The annulus is made of the same metal as said outer metal capsule. One or more low-profile welds are formed around the central circumference of the outer metal capsule for attaching the outer metal capsule to the annulus and for sealing the outer metal capsule. A plurality of substrate particles each having bound thereto a radioisotope are positioned in the outer metal capsule so that the radioisotope is distributed symmetrically within the source, equally divided between the two ends of the source, and positioned with a strong bias towards the extremes of the two ends of the source.

25 Claims, 2 Drawing Sheets

ENCAPSULATED LOW-ENERGY BRACHYTHERAPY SOURCES

CROSS-REFERENCE TO RELATED APPLICATION

This application claims the benefit of U.S. Provisional Application No. 60/074,550, filed Feb. 12, 1998.

BACKGROUND OF THE INVENTION

The invention relates to brachytherapy, which is a specialty within the medical field of radiation oncology. More particularly, it relates to the designs of the small radioactive sources used in interstitial brachytherapy.

Such sources are surgically implanted, temporarily or permanently, in close proximity to diseased tissue about to undergo treatment by the radiation emissions from the sources. Usually, a brachytherapy procedure involves many sources implanted throughout the affected tissue mass. (Note: the prefix brachy in the word brachytherapy is from the Greek work brachys, meaning close or short).

Interstitial brachytherapy sources may be of solid, unitary construction and entirely composed of bio-compatible materials, or they may be composed of radioactive and other materials sealed inside bio-compatible capsules or coatings. Outwardly, they are usually metal cylinders with dimensions in the ranges: length 2 to 5 millimeters and diameter 0.2 to 1 millimeters. They rely for their effectiveness upon the photon radiations, i.e. X-rays and gamma-rays, emitted by certain radioisotopes. The amount of radioactivity contained by each source can vary from 0.1 to 100 millicuries (mCi) but is usually in the range 0.5 to 10 millicuries.

Brachytherapy has been practiced since early this century, starting shortly after the discovery of radium by the Curies in 1898. Many different source types have been developed over the intervening years. These have been based upon radioisotopes widely ranging in their half-lives and emission energies, and manufacturing processes have correspondingly varied. Over the last few decades, most sources have been made by irradiating preformed, solid, unitary "seeds" with neutrons in nuclear reactors. (Note: finished interstitial brachytherapy sources ready for implant are often called seeds, but here the word seed is used in the sense of a preformed solid substrate which is not yet made radioactive to any degree, or is in the process of being made fully radioactive for purposes of making a finished brachytherapy source). This simple and economical approach yields unencapsulated radioactive sources in batch sizes on the order of 10,000 units ready for use without further processing. The most prevalent of this type have been iridium-192 sources, which are made from iridium-platinum alloy seeds. These are generally employed as temporary implants. Although somewhat in decline because the energies of their emissions are now considered to be higher than desirable for many applications, iridium-192 sources are still used in the largest numbers in interstitial brachytherapy.

Within the last ten years, other trends have become clearly apparent. There are strong preferences developing in favor of permanent implant sources and radioisotopes emitting only low-energy photon radiations and having half-lives in the 10 to 100 day range. The main reasons for the change in outlook are: a) permanent implants involve only a single surgical procedure and result in lower hospital costs because of short patient stays with no delays or returns for implant removals; b) low photon energies mean less penetrating power, leading to less radiation exposure of healthy tissue surrounding the diseased tissue region, as well as greatly reduced cumulative radiation doses to hospital personnel; and c) half-lives in the 10 to 100 day range allow the right amount of radiation to be delivered at a rate close to optimum with respect to therapeutic effect.

The two main low-energy sources in commercial supply, and now dominating the overall brachytherapy source market in monetary terms, are encapsulated types with radioactive contents sealed inside welded titanium capsules. One type is base don the radioisotope palladium-103 (half-life 17 days) and the other on iodine-125 (half-life 60 days). Of all radioisotopes, these two appear to be by far the most suited for interstitial brachytherapy applications and are not likely to be easily supplanted. Although these source types do possess the virtues delineated for low-energy sources in the preceding paragraph, both are far from ideal in other important respects: a) both are much more expensive and physically larger than the sources being displaced; b) the encapsulation material strongly attenuated the low-energy radiation output; and c) because they are essentially quasi line sources (as opposed to theoretical line sources which have length but no thickness) and their emissions are of low-energy, their radiation output distributions are anisotropic (i.e. lacking in equality in all directions) and this negatively effects treatment planning and outcome. These deficiencies stem largely from their designs and manufacturing methods.

The sequestering and encapsulation of radioactive materials in small containers for brachytherapy purposes are described in U.S. Pat. Nos. 1,753,287; 3,351,049; 4,323,055; 4,702,228; 4,891,165; 4,994,013; 5,342,283; and 5,405,309, which patents are incorporated herein by reference. With the exception of U.S. Pat. No. 1,753,287, these description taken together summarize the technologies developed to date or formally envisioned for the commercial, large scale production of low-energy brachytherapy sources based on palladium-103 and iodine-125.

With regard to the more prevalent low-energy brachytherapy source types, the structures and degrees of anisotropy are indicated in Chapter 1 of the textbook "Interstitial Brachytherapy—Physical, Biological and Clinical Considerations", Interstitial Collaborative Working Group, Raven Press, New York (1990), ISBN 0-88167-581-4. This textbook is incorporated herein by reference. The output radiation fluxes are shown to fall away steeply at the ends of the sources, caused by absorption of the low-energy photon radiations within the sources themselves. Much of this effect stems from a feature of all real line sources. Descriptively, this feature is the longer average path through the substrate and/or encapsulation materials that must be traveled by the radiation directed towards the ends of real line sources. In the cases of currently available encapsulated low-energy brachytherapy sources, the problem is exacerbated by the fact that the sources are welded at the ends, thereby thickening the capsule walls at these locations.

It should be noted that anisotropy of radiation output is generally not a problem as far as treating tissue lying very close to a low-energy brachytherapy source is concerned. At short distances from the source in any direction, say less than one source length, sufficient radiation dose is delivered regardless of anisotropy. However, the radiation flux diminishes quickly with distance from a source and anisotropy becomes an important factor further out from an implanted source where the radiation dose delivered is calculated to be just adequate for that source to play its part in killing the treated tissue mass. The problem is further complicated when there are large uncertainties in planned treatment parameters caused by variations in the degree of anisotropy between individual sources and uncertainties in the orientation of individual sources within an array of sources.

The problem of anisotropy and the contribution to it by end welds and other sorts of seals was appreciated by the patentees of U.S. Pat. Nos. 3,351,049 and 4,323,055 in relation to iodine-125 sources. These related disclosures envisioned cylindrical metal capsules having closed, rounded ends, with the walls at the ends being smooth and symmetric and having a thickness similar to the side walls. However, this idealized construction was never realized in routine practice, the ends of the production sources being simply sealed by thick bead welds.

Some progress in the area was described in U.S. Pat. Nos. 4,702,228 and 5,405,309 respectively in relation to palladium-103 sources. These related disclosures propose the use of metal tube capsules with laser welded end caps, the tube wall and end cap thicknesses being similar. As well as having thin walled welded end caps, the radioactivity distribution is not uniform along the length, but is somewhat biased towards the ends, which should also promote isotropy at the ends. But again, good isotropy is not evident in these sources. Another capsule designed with improved source isotropy in mind is described in U.S. Pat. No. 4,891,165. This disclosure described cylindrical metal capsules formed by press fitting together two, three or four tightly inter-fitting sleeves, each with one end open and one end closed, to yield finished capsules with laminated walls of essentially uniform thickness all around. As disclosed, the capsules were designed to have flat closed ends and to be optionally sealed by an adhesive or by welding. In practice, two sleeves are used and the design has been modified to have rounded ends. The capsule is used with an internal iodine-125 substrate that distributes the radioactivity uniformly along the length of the source as described in U.S. Pat. No. 4,994,013. The modified design is a means of achieving an essentially cylindrical capsule that has uniform wall thickness all around and to have rounded, smooth, symmetric, closed ends as originally disclosed in U.S. Pat. No. 3,351,049. In practice, the capsule of U.S. Pat. No. 4,891,165 is sealed by performing a circumferential weld close to one end where the rim of the formerly open end of the outer cylinder rests against the side wall of the inner cylinder. A study reported in Medical Physics, Vol. 19, No. 4, pp. 927–931 (1992), incorporated herein by reference, indicates that a significant improvement in isotropy is gained by means of this technology, although it is not clear whether welded or non-welded capsules were used in the study. There are perceived problems with this technology, however. Because of the lack of a heat sink behind the weld area, there is a high potential for severely weakening or even perforating the capsule wall in performing the circumferential weld. Another perceived problem due to the lack of a heat sink behind the weld area, is the heating of the internal radioactive substrates, resulting in releases of volatile radioactive iodine and blow-outs during welding before the seal is complete. Yet another perceived problem is that the weld is near one end of the source, resulting in some contribution to source anisotropy because of attenuation of the low-energy radiation.

SUMMARY OF THE INVENTION

The present invention provides new designs for radioactive sources which are meant primarily for implantation within the human body for purposes of brachytherapy. The invention addresses the anisotropy problems associated with encapsulated, generally cylindrical, low-energy sources. The new designs allow for a higher degree of isotropy of radiation output to be attained relative to similar sources currently commercially available. This is achieved by positioning the spherical substrate beads carrying the radioactive material close to the thin walled, rounded ends of a source; and by sealing the source with a weld around the central circumference.

In accordance with a broad aspect of the invention, there is provided an essentially cylindrical, metal-encapsulated, brachytherapy source comprising an outer metal capsule, an annulus in a central interior position of the outer metal capsule, and a longitudinally extending heavy metal core in the annulus. The annulus is made of the same metal as the outer metal capsule. Means including one or more low-profile welds are provided around the central circumference of the outer metal capsule for attaching the outer metal capsule to the annulus and for sealing the outer metal capsule. A plurality of substrate particles each having bound thereto a radioisotope are positioned in the outer metal capsule so that the radioisotope is distributed symmetrically within the source, equally divided between the two ends of the source, and positioned with a strong bias towards the extremes of the two ends of the source. Also, the length of the metal core is determined by the shape, size and number of substrate particles at each end of the source.

In accordance with another broad aspect of the invention, there is provided a metal-encapsulated brachytherapy source comprising an elongated plug having an essentially cylindrical portion defining an elongated axis; an outer metal capsule including two metal end-tubes aligned along the longitudinal axis with each one of the end-tubes having one closed end facing outwardly of the source and one open end tightly fitted on the plug and facing inwardly. Each one of the end-tubes are welded to the plug with a space between the closed end thereof and a respective end of the plug. Also, at least one substrate including at least one radioisotope is in the space in each one of the end-tubes.

In accordance with a specific aspect of the invention, the plug comprises an elongated annulus and a heavy metal core within the annulus. Also, the annulus is made of the same metal as the outer metal capsule.

In accordance with another specific aspect of the invention, there is a plurality of substrate particles in each one of the spaces in the end-tubes with the radioactivity intensity decreasing from the outer end to the inner end of each space. In one embodiment, there are two substrate particles in each one of the spaces in the end-tubes with the radioactivity of the outer substrate particle being twice the radioactivity of the inner substrate particle.

A broad object of the invention is to provide safe, effective, cylindrically encapsulated, low-energy brachytherapy sources with improved isotropy of radiation output relative to currently available sources of the same general type.

A specific objective of the invention is to address anisotropy by strongly biasing the position of the radioactive components towards the ends of the sources, thereby compensating for the radiation attenuation that takes place in the capsule walls of currently available sources.

Another specific objective of the invention is to provide better symmetry of radiation output, and better reliability of capsule integrity, by providing a better situation for the sealing weld of the source capsules relative to other source designs.

DESCRIPTION OF THE PREFERRED EMBODIMENTS

In a preferred embodiment, the capsule materials are titanium and platinum-iridium alloy metals, the substrates holding the radioactive material are spherical beads composed of a zeolite with a binder, and the radioisotope is either palladium-103 or iodine-125.

Figure 1:
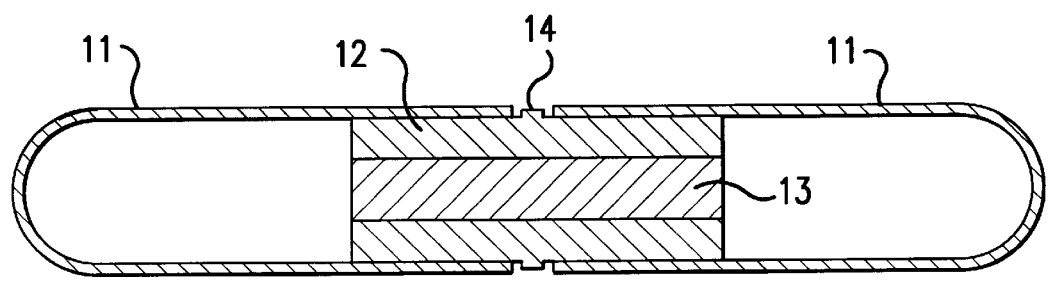
FIG. 1 shows an unwelded source capsule assembled without contents.

FIG. 1 shows the assembled but unwelded components of the metal capsule. The capsule is composed of three parts: two identical titanium end-tubes 11 with one open end and one closed rounded end; and one cylindrical, annular titanium plug 12 with a concentric platinum-iridium alloy core 13, onto each end of which the end-tubes are press fitted. The annular titanium plug has a central circumferential ridge 14 with a low profile. The ridge serves as a stop and as an alignment aid in the attachment of the end-tubes, and provides extra titanium at the weld location.

Figure 2:
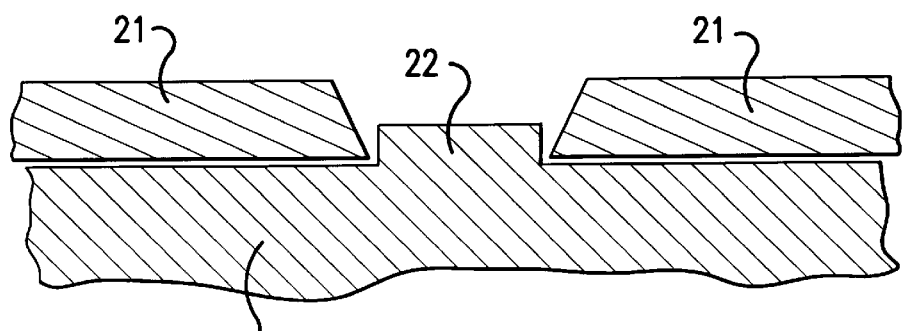
FIG. 2 shows detail of the weld region of the capsule of FIG. 1.

FIG. 2 is a magnified view of the weld region of the source showing the end-tube walls 21 butted against the ridge 22 of the annular plug 23.

Figure 3:
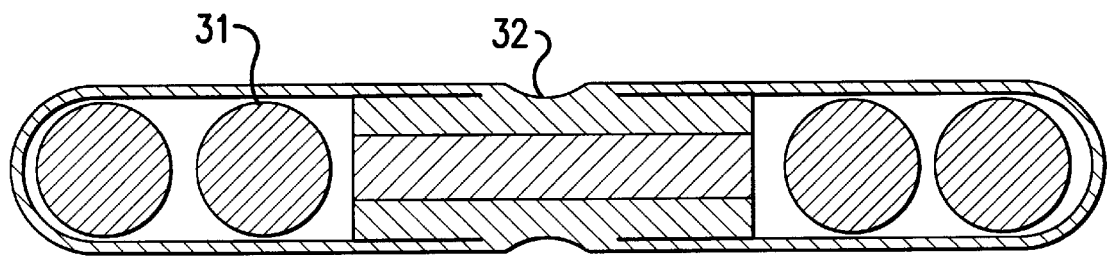
FIG. 3 shows a welded source containing four radioactive substrate beads.

FIG. 3 shows a welded source with four zeolite bead substrates 31. The radioactive ingredient is symmetrically distributed within the source and is firmly attached to the zeolite beads by chemical bonding or physical entrapment. A single circumferential weld 32 is performed to secure the end tubes to the annulus and to each other, and to hermetically seal the finished source.

Figure 4:
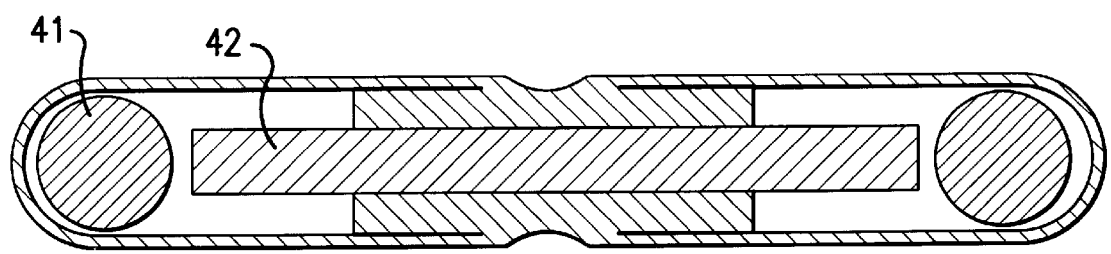
FIG. 4 shows a welded source containing two radioactive substrate beads.

FIG. 4 shows a source with two zeolite bead substrates 41. The platinum-iridium alloy core 42 length is chosen to limit the free space available for the movement of the zeolite beads within the capsule, depending on whether two or four zeolite beads per source are used.

The titanium annulus 12,23 provides good backing for the weld and thus helps in avoiding capsule wall perforation in the welding process. The titanium annulus 12,23 and platinum-iridium alloy core 13,42 together have sufficient bulk to provide a heat sink to curb the temperature excursion experienced by the radioactive components during source welding. Thus, the probability of volatilization and blow-out of certain radioisotopes, such as iodine-125, is reduced. The location of the weld 32 minimizes the effect of the weld on symmetry and uniformity of radiation output caused by photon absorption in the weld bead. The heavy platinum-iridium alloy core 13,42 of the annulus acts as a linear X-ray marker for detection of the source and determination of its orientation from outside the body after implantation. The uniform wall thickness of the capsule and the close fit of the spherical bead substrates 31,41 in the end tubes promote symmetry and stability respectively of the radiation output. The heavy positional bias of the radioactivity towards the ends of the capsule promotes good isotropy relative to similar sources by compensating for attenuation of radiation in the capsule wall. The option of four substrate beads as opposed to two allows an increase in source strength. This option also allows for adjustment in the degree of radiation isotropy by changing the ratio of the amount of radioactivity on the inner pair of beads versus the amount on the outer pair.

In the matter of dimensions, the sources of FIGS. 3 and 4 may vary in length between 3 and 10 millimeters and in diameter between 0.5 and 1.5 millimeters. The uniform wall thickness of the end tubes may vary between 0.02 and 0.2 millimeters. The dimensions of the other components are made to a close fit. Generally, the diameter of the spherical substrates may vary between 0.3 and 1.3 millimeters.

Zeolites are a class of crystalline molecular sieves that occur naturally or can be synthesized in powder form. They are thermally stable inorganic compounds that have an open alumino-silicate framework that allows them to host other chemical species within their structures. Their relevant properties include: good heat and radiation resistance; cation exchange capacities comparable with organic resins; good capacities for the adsorption and retention of various radioactive iodine species; low density and average atomic number of elemental constituents meaning low attenuation of low-energy photons; and with a binder can be formed into durable pellets or spherical beads in appropriate sizes. For comprehensive information on zeolites and their applications, the reader is referred to the textbook "Zeolite Molecular Sieves" by Donald W. Breck, John Wiley and Sons Inc., New York (1974), which textbook is incorporated herein by reference.

PROPHETIC EXAMPLE

It is intended to produce one hundred titanium-encapsulated interstitial brachytherapy sources each containing six millicuries of palladium-103 radioactivity. The palladium-103 in each source is to be divided between four zeolite bead substrates distributed as follows: two millicuries on each outer bead and one millicurie on each inner bead. The sources are to have dimensions as follows: length 4.5 millimeters; diameter 0.8 millimeters, and end-tube wall thickness 0.05 millimeters.

A large bath of 4A type zeolite beads having bead diameters of 0.65 millimeters is previously acquired. Large batches of each of the capsule parts are acquired in the following dimensions: end-tube, 2.2 millimeters in length, 0.8 millimeters in outer diameter, 0.05 millimeters in wall thickness; and titanium/platinum-iridium alloy annular plugs, 1.7 millimeters in length, 0.7 millimeters in body diameter, core diameter 0.3 millimeters, ridge diameter 0.75 millimeters, and ridge width 0.1 millimeters. The annular plugs are sized to fit snugly into the end tubes so that when press fitted the two pieces do not easily part.

A sub-batch of at least two hundred of the 4A zeolite beads is suitably immersed in and mixed with an aqueous solution of palladium-103 in ammonium hydroxide at a pH of 10.5 so as to evenly load 2 millicuries of palladium-103 onto each bead. The beads are then separated from the solution and thoroughly dried in a drying oven, first at 100 degrees Celsius for 1 hour and then at 350 degrees Celsius for 1 hour. Another sub-batch of at least two hundred of the zeolite beads is taken and similarly treated so as to yield dry zeolite beads each loaded with 1 millicurie of palladium-103.

A zeolite bead loaded with 2 millicuries of palladium-103 is dispensed into each of two hundred titanium end-tubes held in a vertical orientation with the open ends uppermost. Then a zeolite bead loaded with 1 millicurie of palladium-103 is dispensed into each of the same two hundred end-tubes, so that a 1 millicurie bead rests on top of each 2 millicurie bead. A titanium annular plug with a platinum-iridium alloy core is then pressed firmly into each of the open ends of one hundred of the end-tubes into which the zeolite beads have been dispensed. The pressure used is just sufficient to ensure that the perimeter of the previously open end of the end-tube rests squarely against the ridge stop on the annular plug. The one-hundred plugged end-tubes are then inverted and each is pressed, protruding annular plug first, into one of the remaining one hundred unplugged end-tubes. Each of the one hundred assembled sources is then laser welded under argon atmosphere to provide a hermetic seal around the circumference where the previously open ends of the two end-tubes and the ridge of the annular plug meet. The sources are then ready for surface cleaning, inspection and testing before shipment to medical centers.

Other bio-compatible materials, such as stainless steel, are useable as material for the construction of the source capsule. Other heavy metals, such as gold, silver, tantalum, tungsten and the six platinum elements, and alloys of these elements are useable in place of platinum-iridium alloy as the X-ray marker material. Other materials such as carbon, charcoal and ion-exchange resins in spherical bead or other particulate form are useable as substrate material for the radioisotope. Other radioisotopes such as cesium-131, samarium-145, terbium-161 and thulium-170 are useable.

Variations in design might be advanced to achieve the central circumferential weld and a similar distribution of radioactivity within a similarly shaped source. The invention contemplates and encompasses all such variations.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. An essentially cylindrical, metal-encapsulated, brachytherapy source comprising:
    an outer metal capsule, an annulus in a central interior position of said outer metal capsule, and a longitudinally extending heavy metal core in said annulus; said annulus being made of the same metal as said outer metal capsule;
    means including one or more low-profile welds around the central circumference of said outer metal capsule for attaching said outer metal capsule to said annulus and for sealing said outer metal capsule;
    a plurality of substrate particles each having bound thereto a radioisotope, said substrate particles being positioned in said outer metal capsule so that the radioisotope is distributed symmetrically within the source, equally divided between the two ends of the source, and positioned with a strong bias towards the extremes of the two ends of the source; and
    the length of said metal core being determined by the shape, size and number of substrate particles at each end of the source.

2. The source of claim 1 wherein said outer metal capsule and said annulus is formed of titanium or a titanium alloy.

3. The source of claim 1 wherein said core of said annulus is made of platinum-iridium alloy metal.

4. The source of claim 1 wherein said substrate particles are two zeolite spheres.

5. The source of claim 1 wherein said substrate particles are four zeolite spheres.

6. The source of claim 1 wherein said radioisotope is palladium-103.

7. The source of claim 1 wherein said radioisotope is iodine-125.

8. A metal-encapsulated brachytherapy source comprising;
    an elongated plug having an essentially cylindrical portion defining an elongated axis;
    an outer metal capsule including two metal end-tubes aligned along said longitudinal axis with each one of the end-tubes having one closed end facing outwardly of said source and one open end tightly fitted on said plug and facing inwardly, each one of the end-tubes being welded to said plug with a space between the closed end thereof and a respective end of said plug; and
    at least one substrate including at least one radioisotope is in the space in each one of the end-tubes.

9. The source of claim 8 wherein both of the open ends are bonded to said plug by a single circumferential weld.

10. The source of claim 8 wherein the closed ends of the end-tubes are rounded.

11. The source of claim 8 wherein said plug comprises an elongated annulus and a heavy metal core within the annulus.

12. The source of claim 11 wherein said annulus is made of the same metal as said outer metal capsule.

13. The source of claim 11 wherein said annulus and said outer metal capsule are titanium or a titanium alloy.

14. The source of claim 13, wherein said core is made of a material selected from the group consisting of platinum-iridium alloy metal, gold, silver, tantalum, tungsten, the six platinum elements, and alloys thereof.

15. The source of claim 14, wherein said annulus has a central circumferential ridge with a low profile (1) for serving as a stop and as an alignment aid when attaching the end-tubes, and (2) for providing extra titanium during welding.

16. The source of claim 15, wherein said annulus is formed of the same material as said outer metal capsule.

17. The source of claim 8 wherein each one of the two end-tubes are sealed to said plug by one or more low-profile welds around the circumference of each one of the two end-tubes.

18. The source of claim 8 wherein each substrate has the radioisotope bound thereto such that the radioisotope is distributed symmetrically within the source, equally divided between the two ends of the source, and positioned with a strong bias towards the extremes of the two ends of the source.

19. The source of claim 8 wherein each one of the spaces has one substrate of a zeolite sphere.

20. The source of claim 8 wherein each one of the spaces has two substrates of zeolite spheres.

21. The source of claim 8 wherein said radioisotope is palladium-103.

22. The source of claim 8 wherein said radioisotope is iodine-125.

23. The source of claim 8 wherein there is a plurality of substrate particles in each one of the spaces in the end-tubes with the radioactivity intensity decreasing from the outer end to the inner end of each space.

24. The source of claim 8 wherein there are two substrate particles in each one of the spaces in the end-tubes with the radioactivity of the outer substrate particle being twice the radioactivity of the inner substrate particle.

25. The source of claim 8 wherein the outer surface of said plug is made of the same metal as said outer metal capsule.

* * * * *